US010032614B2

(12) United States Patent
Baba et al.

(10) Patent No.: US 10,032,614 B2
(45) Date of Patent: Jul. 24, 2018

(54) METHODS FOR ANALYSIS OF LIPIDS USING MASS SPECTROMETRY

(71) Applicant: DH Technologies Development PTE Ltd., Singapore (SG)

(72) Inventors: Takashi Baba, Richmond Hill (CA); John Lawrence Campbell, Milton (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/316,915

(22) PCT Filed: Jun. 4, 2015

(86) PCT No.: PCT/IB2015/054236
§ 371 (c)(1),
(2) Date: Dec. 7, 2016

(87) PCT Pub. No.: WO2015/189749
PCT Pub. Date: Dec. 17, 2015

(65) Prior Publication Data
US 2017/0117124 A1    Apr. 27, 2017

Related U.S. Application Data

(60) Provisional application No. 62/012,257, filed on Jun. 13, 2014.

(51) Int. Cl.
*G01N 33/92* (2006.01)
*H01J 49/00* (2006.01)
*H01J 49/42* (2006.01)

(52) U.S. Cl.
CPC ...... *H01J 49/0054* (2013.01); *H01J 49/0072* (2013.01); *H01J 49/4225* (2013.01)

(58) Field of Classification Search
CPC .. G01N 33/92; H01J 49/0072; H01J 49/0027; H01J 49/0045; H01J 49/0054
(Continued)

(56) References Cited

U.S. PATENT DOCUMENTS 9,202,678 B2 * 12/2015 Dantus ............... H01J 49/0059
9,347,917 B2 *  5/2016 Campbell ........... H01J 49/0031
(Continued)

FOREIGN PATENT DOCUMENTS

JP    2007064950 A    3/2007

OTHER PUBLICATIONS

International Search Report and Written Opinion for PCT/IB2015/054236 dated Aug. 28, 2015.
(Continued)

*Primary Examiner* — David A Vanore

(57) ABSTRACT

A method and apparatus for analyzing samples using mass spectrometry are disclosed. The apparatus includes a reaction device configured to dissociate sample ions into fragments by reacting the sample ions with a charged species (e.g., electrons) such as through ECD, EID, or EIEIO. The kinetic energy of the charged species is such that the fragments may be detected and produce spectra that allow for the determination of isomeric species in the sample and the location of double bonds of sample molecules. The fragments may include radical fragments and non-radical fragments. The apparatus may also include an oxygen gas source configured to react with the radical fragments to produce oxygen-radical fragments. Spectra resulting from analysis of the fragments may allow for the determination of the oxygen-radical fragments resulting from the dissociation of the sample molecules.

21 Claims, 9 Drawing Sheets

(58) Field of Classification Search
USPC ... 250/281, 282, 288, 283, 424, 307, 423 R, 250/427; 435/134; 315/111.81
See application file for complete search history.

(56) References Cited

U.S. PATENT DOCUMENTS

| | | | |
|---|---|---|---|
| 2004/0232324 A1 | 11/2004 | Berkout et al. | |
| 2007/0114384 A1* | 5/2007 | Berkout | H01J 49/0045 250/287 |
| 2007/0164212 A1* | 7/2007 | Ogata | G01N 30/8675 250/288 |
| 2008/0073500 A1 | 3/2008 | Cerda et al. | |
| 2010/0167267 A1* | 7/2010 | Schulzknappe | G01N 33/6848 435/5 |
| 2010/0200742 A1* | 8/2010 | Schultz | H01J 49/0045 250/252.1 |
| 2011/0295521 A1* | 12/2011 | Satulovsky | H01J 49/0036 702/28 |
| 2013/0306853 A1* | 11/2013 | Eastwood | H01J 49/0036 250/282 |
| 2014/0027631 A1* | 1/2014 | Trimpin | H01J 49/165 250/282 |
| 2014/0374591 A1* | 12/2014 | Campbell | H01J 49/10 250/283 |
| 2015/0260684 A1* | 9/2015 | Blanksby | G01N 27/622 250/288 |
| 2016/0013037 A1* | 1/2016 | Jorabchi | H01J 49/105 73/23.37 |
| 2017/0084437 A1* | 3/2017 | Jackson | H01J 49/0072 |
| 2017/0117124 A1* | 4/2017 | Baba | H01J 49/0054 |

OTHER PUBLICATIONS

Hyun Ju Yoo et al: "Determination of Double Bond Location in Fatty Acids by Manganese Adduction and Electron Induced Dissociation", Analytical Chemistry, vol. 82, No. 16, Aug. 15, 2010, pp. 6940-6946 US.

* cited by examiner

| Head group | | | | | | | |
|---|---|---|---|---|---|---|---|
| 184.0728 m/z | 142.0258 m/z | 207.9978 m/z | 283.0188 m/z | | | | |
| PC | PE | PS:sodiated | PI:sodiated | | | | |
| sn2 diagnostic m/z | | | | sn2 | | (precursor m/z) - (sn2 diagnostic m/z) | sn1 |
| 549.415 | 507.368 | 573.340 | 648.361 | 22:0 | | 353.342 | 22:0 |
| 547.399 | 505.352 | 571.324 | 646.345 | 22:1 | | 351.326 | 22:1 |
| 545.384 | 503.337 | 569.309 | 644.330 | 22:2 | | 349.310 | 22:2 |
| 543.368 | 501.321 | 567.293 | 642.314 | 22:3 | | 347.295 | 22:3 |
| 541.353 | 499.306 | 565.278 | 640.299 | 22:4 | | 345.279 | 22:4 |
| 539.337 | 497.290 | 563.262 | 638.283 | 22:5 | | 343.264 | 22:5 |
| 537.321 | 495.274 | 561.246 | 636.267 | 22:6 | | 341.248 | 22:6 |
| 535.399 | 493.352 | 559.324 | 634.345 | 21:0 | | 339.326 | 21:0 |
| 533.384 | 491.337 | 557.309 | 632.330 | 21:1 | | 337.310 | 21:1 |
| 531.368 | 489.321 | 555.293 | 630.314 | 21:2 | | 335.295 | 21:2 |
| 521.384 | 479.337 | 545.309 | 620.330 | 20:0 | | 325.310 | 20:0 |
| 519.368 | 477.321 | 543.293 | 618.314 | 20:1 | | 323.295 | 20:1 |
| 517.353 | 475.306 | 541.278 | 616.299 | 20:2 | | 321.279 | 20:2 |
| 515.337 | 473.290 | 539.262 | 614.283 | 20:3 | | 319.264 | 20:3 |
| 513.321 | 471.274 | 537.246 | 612.267 | 20:4 | | 317.248 | 20:4 |
| 507.368 | 469.259 | 535.231 | 610.252 | 19:0 | | 311.295 | 19:0 |
| 505.353 | 465.321 | 531.293 | 606.314 | 19:1 | | 309.279 | 19:1 |
| 493.353 | 451.306 | 517.278 | 592.299 | 18:0 | | 297.279 | 18:0 |
| 491.337 | 449.290 | 515.262 | 590.283 | 18:1 | | 295.264 | 18:1 |
| 479.337 | 437.290 | 503.262 | 578.283 | 17:0 | | 283.264 | 17:0 |
| 477.321 | 435.274 | 501.246 | 576.267 | 17:1 | | 281.248 | 17:1 |
| 465.321 | 423.274 | 489.246 | 564.267 | 16:0 | | 269.248 | 16:0 |
| 463.306 | 421.259 | 487.231 | 562.252 | 16:1 | | 267.232 | 16:1 |
| 451.306 | 409.259 | 475.231 | 550.252 | 15:0 | | 255.232 | 15:0 |
| 449.290 | 407.243 | 473.215 | 548.236 | 15:1 | | 253.217 | 15:1 |

METHODS FOR ANALYSIS OF LIPIDS USING MASS SPECTROMETRY

RELATED APPLICATIONS

This application claims the benefit of priority from U.S. Provisional Application No. 62/012,257, filed on Jun. 13, 2014, the entire contents of which is herein incorporated by reference.

FIELD

The invention generally relates to mass spectrometry, and more particularly to methods and apparatus for the analysis of lipids involving the detection of isomeric lipids and/or the location of double bonds within a lipid molecule.

INTRODUCTION

Mass spectrometry (MS) is an important tool for the quantification and structural analysis of organic compounds. Advanced techniques have been developed to analyze larger and more complex molecules by dissociating molecules into smaller fragments within a mass spectrometer or a tandem spectrometer (MS/MS) prior to detection. Analysis of the fragments may provide detailed structural information unavailable through examination of the complete molecules. Various techniques have been developed for inducing dissociation. One early example is collision induced dissociation (CID) in which sample ions are contacted with gas atoms or molecules to induce dissociation. Another example is electron capture dissociation (ECD) in which sample molecules are contacted with electrons having a kinetic energy of about 0 electron Volts (eV) to about 3 eV (also referred to as "hot" ECD (HECD)) for electrons having a kinetic energy above about 5 eV to about 10 eV). In ECD, sample ions are fragmented as the sample ion captures an electron and charge neutralization occurs at the capture site, leading to an excited radical species that undergoes bond cleavage. ECD has been adapted to analyze smaller charged ions by increasing the electron kinetic energy above 3 eV, referred to as electron induced dissociation (EID). Other reported dissociation techniques include electron transfer dissociation (ETD) using reagent anions and electron detachment dissociation (EDD) using electrons with kinetic energy of greater than 3 eV. Proton transfer reactions (PTR) can also be utilized to reduce the charge state of ions in which a proton is transferred from one charged species to another.

Dissociation techniques have proven to be very useful for MS analysis of organic compounds, including bio-molecular species such as peptides, proteins, glycans, and post translationally modified peptides/proteins. However, substantial limitations remain for MS analysis of certain types of molecular samples and structural details thereof. For example, traditional mass spectrometry techniques are sometimes inadequate to discriminate between two or more isomeric species in a sample. Such information is often significant because, despite the structural similarity of isomeric species, their biological activity can vary drastically. Moreover, the presence of a particular isomer and/or the relative abundance of the isomers can be important for medical diagnostics. For example, regioisomers are molecules that contain the same core structure and side chains, though the side chains can be arranged in more than one position. Certain regioisomers can serve as critical biomarkers for disease and/or provide information regarding underlying biomolecular activity based, for instance, on the relative abundance of the various regioisomers in tissues (i.e., brain vs. kidney). However, conventional MS-based techniques have not been able to generate mass spectra with adequate information and decreased complexity to allow for resolution of the isomeric species for many regioisomer samples.

An illustrative regioisomer sample involves the two most common phosphatidylcholine (PC) regioisomers 1-palmatoyl-2-oleoyl-sn-phosphatidylcholine (POPC) and 1-oleoyl-2-palmatoyl-sn-phosphatidylcholine (OPPC).

Although both positive-mode and negative-modes of MS/MS have shown some promise in individually quantifying POPC and OPPC based on the diagnostic fragment ions present in their MS/MS fragmentation spectra, it nonetheless remains difficult to quantify a particular species in a mixture containing both isomers as their fragmentation behavior is essentially identical. Further, no chromatographic separation is presently available. Indeed, when OPPC and POPC are both present, their MS/MS fragmentation spectra are convolved such that these lipid regioisomers are generally analyzed and quantified in tandem (i.e., without enumerating the abundance of each particular isomer). Similarly, many other isomeric lipids, including but not limited to triacylglycerols (TAGs) and diacylglycerols (DGs), are difficult to quantify individually when present in a mixture.

In another example, MS and/or MS/MS techniques are able to generate spectra that allow for the determination of class, carbon chain length, and degree of unsaturation (i.e., double bonds) of lipids. However, determination of the actual carbon-carbon double bond position within a sample molecule has remained elusive. The number and location of double bonds can have a significant bearing on understanding the chemical reactivity or medical importance of a molecule. One technique for identifying the number and location of double bonds in a molecule using MS involves ozone-induced dissociation (OzID), which involves the reaction of ozone with a sample molecule to cleave carbon-carbon double bonds in a specific, characteristic manner. However, in certain analytical conditions, OzID may require manual intervention and prior knowledge of the presence of carbon-carbon double bonds in a sample molecule. High-energy CID has been employed to determine double-bond location within a lipid molecule. However, CID is difficult to employ practically because the technique is not able to efficiently generate diagnostic fragment ions. As such, there is insufficient confidence in the determination of double-bond position from resultant spectra to make the analysis analytically useful.

Accordingly, there remains a need for improved quantitation of isomeric lipids with enhanced discrimination between species and the ability to easily and confidently determine the position of double bonds in an efficient MS or MS/MS work flow.

SUMMARY

Apparatus, systems, and methods in accordance with the applicants' present teachings allow for the analysis of lipids in an analytical sample using mass spectrometry, including determining isomeric species within an isomeric mixture of lipids and the locations of double-bonds within a lipid molecule. Ionized lipid molecules in an analytical sample may be subjected to a dissociation reaction by contacting the ionized lipid molecules with electrons (i.e., an electron beam) within a reaction device of a mass spectrometer to form various fragments of the lipid molecules. The electrons may have a kinetic energy of about 4 electron Volts (eV) to about 12 eV. The fragments may be detected by a detector of the mass spectrometer to generate spectra for the analytical sample. The fragments generated by the dissociation reaction according to applicants' present teachings are conducive to, among other things, discerning lipid isomers in an analytical sample including a mixture of isomers and determining locations of double bonds of lipid molecules in the analytical sample.

In accordance with one aspect, certain embodiments of the applicants' teachings relate to a method for analyzing a sample. According to the method, a sample, for instance, one containing or suspected of containing a plurality of lipid isomers, may be ionized so as to form one or more lipid ions. The method may also include separating the lipid ions. In some embodiments, the lipid ions may be transported through a differential mobility spectrometer to affect their separation.

In some aspects, ionizing the sample may include reacting the sample with a cationization reagent. For example, the cationization reagent may include a salt of any of sodium, potassium, silver, and lithium. In another example, ionizing the sample can comprise reacting the sample with one of silver and lithium.

In various aspects, the lipid isomers can be selected from the group comprising fatty acids, saturated fatty acids, unsaturated fatty acids, glycerolipids, glycerophospholipids, sphingolipids, saccharolipids, polyketides, sterol lipids, prenol lipids, PC, OPPC, and POPC. In some aspects, an acyl or alkyl chain of the lipid isomers may include at least one double bond (i.e., an unsaturated carbon).

In accordance with various aspects of applicants' present teachings, certain embodiments relate to a method of mass spectrometry, comprising exposing a sample comprising a plurality of isomeric lipids to a cationization reagent so as to stabilize a configuration of said plurality of isomeric lipids. The method can further comprise transporting said stabilized isomeric lipids through an ion mobility spectrometer so as to effect separation of said plurality of one or more stabilized isomeric lipids.

In some embodiments, a method for analyzing a sample, for instance, one containing or suspected of containing at least one lipid, using a mass spectrometer may include ionizing the sample to form a plurality of precursor ions, performing an ion-electron reaction to fragment at least a portion of the plurality of precursor ions into a plurality of fragment ions, the ion-electron reaction comprising irradiating the plurality of precursor ions with a charged species to cause fragmentation of two isomeric forms of a lipid (if present in the sample) into the fragment ions such that the fragmentation pattern associated with one isomer is different from the fragmentation pattern associated with the other isomer, and detecting at least a portion of the plurality of fragment ions at a detector of the mass spectrometer to form at least one spectrum for mass analysis of the sample.

In some embodiments, a method for analyzing a sample containing or suspected of containing at least one lipid using a mass spectrometer may include ionizing the sample to form a plurality of singly-charged precursor ion species, performing an ion-electron reaction to fragment at least a portion of the plurality of precursor ion species into a plurality of product ion species, the ion-electron reaction comprising irradiating the plurality of product ions with electrons having a kinetic energy of about 4 eV to about 12 eV; and detecting at least a portion of the plurality of product ion species at a detector of the mass spectrometer to form at least one spectrum for mass analysis of the sample.

In various aspects, the electrons may have a kinetic energy of about 3 eV, 4 eV, about 5 eV, about 6 eV, about 7 eV, about 8 eV, about 9 eV, about 10 eV, about 11 eV, about 12, eV, about 13 eV, about 14 eV, about 15 eV, about 16 eV, about 17 eV, about 18 eV, about 19 eV, about 20 eV, and any value or range between any two of these values (including endpoints). In various aspects, the electrons may have a kinetic energy of about 4 eV to about 12 eV. In some aspects, the electrons may have a kinetic energy of about 5 eV to about 8 eV.

In some embodiments, the ion-electron reaction may include electron capture dissociation (ECD), hot electron capture dissociation (HECD), electron transfer dissociation (ETD), electron ionization dissociation (EID), electron-induced excitation of ions in organics (EIEIO), and electron detachment dissociation (EDD). In EIEIO, while no electron capture event occurs analyte ions (generally singly charged) are subjected to electric and vibrational excitation leading to the formation of distinct fragment ions. In some embodiments, the ion-electron reaction may be implemented in a flow-through mode or a trapping mode. In some embodiments, the ion-electron reaction may occur in a Fourier transform ion cyclotron resonance cell, a digital Paul trap, a linear ion trap, and a Chimera trap (as described herein below).

In various aspects, methods of analyzing samples according to applicants' present teachings may generate spectra for the molecules within the sample. Double bonds of analyzed lipids may be indicated on the spectra according to a spacing of the plurality of fragment ions. In various aspects, a 14 atomic mass unit (amu) spacing may indicate a single bond and a 12 amu spacing may indicate a double bond.

In various aspects, methods of analyzing samples according to applicants' present teachings may generate spectra that allow for determination of isomeric species. For example, the spectra may show the relative intensity of unique fragments of isomeric species. The relative intensity may indicate the relative abundance of the isomeric species.

In various aspects, the plurality of fragment ions may include radical fragments and non-radical fragments. In some aspects, for each dissociation site on a molecule, corresponding radical fragments and non-radical fragments may appear pairwise on a spectrum generated according to some embodiments.

In various aspects, a gas may be introduced to react with radical fragments of the fragmented lipid molecules. In some embodiments, the gas may include oxygen, nitrogen, or helium. In some embodiments, the gas may be introduced within the ion-electron reaction device. In some embodiments, the gas may be introduced downstream of the ion-electron reaction device. In some embodiments, the gas may be introduced for about 1 millisecond to about 100 milliseconds.

In various aspects, on a spectrum, the fragments that reacted with the gas may appears as gas-radical fragment peaks. For instance, in an embodiment in which the gas is oxygen, the fragments that reacted with oxygen may appear as oxygen-radical fragment peaks. The oxygen-radical fragment peaks may correspond with the peak of the non-reacted fragment shifted 32 amu (corresponding to $+O_2$ with the fragment). In various aspects, other gas types would exhibit corresponding amu shifts based on their particular properties. An oxygen-radical fragment peak may indicate which fragments of the lipid molecule are radicals. In various aspects, an oxygen-radical fragment profile may appear as a peak split at a double bond location of an analyzed lipid molecule. In various aspects, the oxygen-radical fragment profile may be used as a redundant check on double bond locations indicated on a spectra of a mass analysis in which oxygen gas was not introduced.

In various aspects, a reaction apparatus for ions may include a first pathway comprising a first axial end and a second axial end disposed at a distance from the first pathway axial end along a first central axis, a second pathway comprising a first axial end and a second axial end disposed at a distance from the first axial end of the second pathway along a second central axis, said first and second central axis being substantially orthogonal to one another and having an intersection point, a first set of quadrupole electrodes being arranged in a quadrupole orientation around said first central axis and disposed between said first axial end of said first pathway and said intersection point, said first set of electrodes for guiding ions along a first portion of said first central axis, a second set of quadrupole electrodes arranged in a quadrupole orientation around said first central axis and disposed between said second axial end of said first pathway and said intersection point, said second set of electrodes for guiding ions along a second portion of said first central axis, the first set of electrodes being separated from the second set of electrodes so as to form a gap transverse to said first central axis, a voltage source for providing an RF voltage to said first and second sets of electrodes to generate an RF field, a controller for controlling said RF voltages, a lipid ion source disposed at or proximate either the first or second axial end of said first pathway for introducing lipid ions along said first central axis towards the other of said first or second axial end of the first pathway, and a charged species source disposed at or proximate either the first or second axial end of the second pathway for introducing electrons having a kinetic energy of about 4 electron Volts to about 12 electron Volts along the second central axis, said charged species travelling through said gap towards said intersection point.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in any way.

DETAILED DESCRIPTION

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

Methods and systems for dissociating lipid ions ("precursor ions") of an analytical sample into fragments ("fragment ions") and analyzing the fragments are provided herein. In accordance with various aspects of the applicants' teachings, the methods and systems can provide for the fragmenting of lipid ions of an analytical sample into fragment ions that may be expressed on an MS spectrum that allows for a detailed determination of the chemical structure of the precursor ions, which may be difficult to achieve with conventional MS techniques. In various aspects, methods and systems in accordance with applicants' teachings can enable a mass spectrometer to resolve a sample's isomeric lipids, such as POPC and OPPC, and/or the location of double bonds of lipid molecules within a sample, all by way of non-limiting example.

Figure 1:
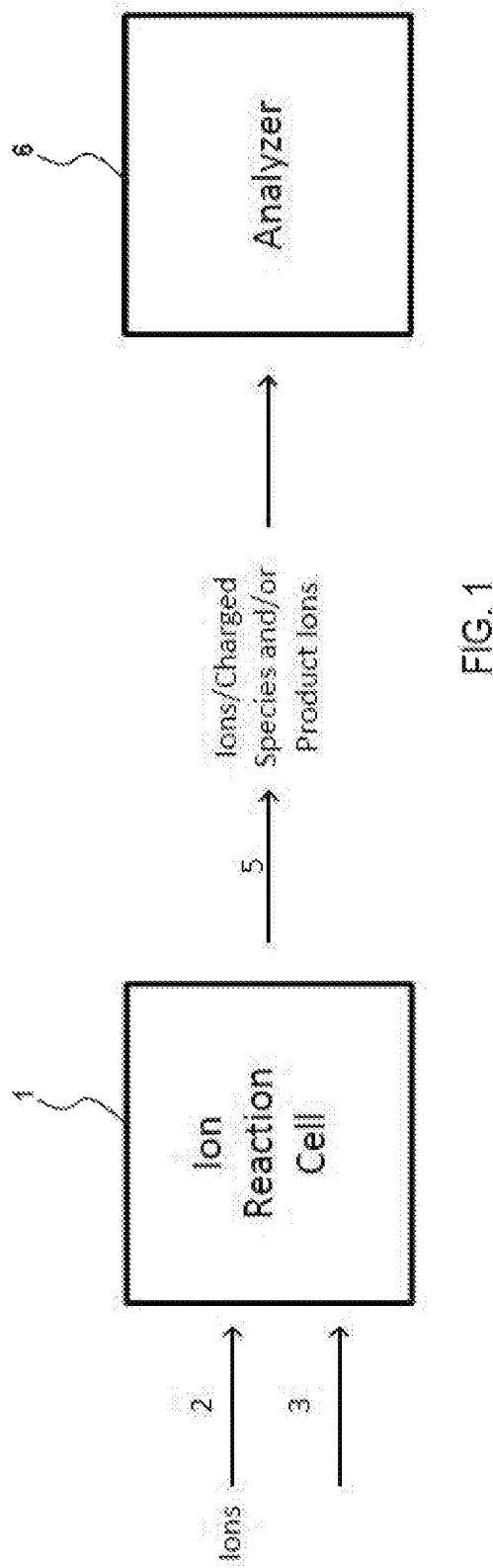
FIG. 1 depicts a schematic view of an implementation of an embodiment of the invention.

Referring to FIG. 1 there is depicted a general schematic diagram of an ion reaction cell configured to perform various aspects of some embodiments. As discussed below, the ion reaction cell can be incorporated within a mass spectrometer in accordance with the present teachings. As shown in FIG. 1, an ion reaction cell 1 may have as inputs a series of reactants including ions 2 and a charged species 3. The ions 2 can be any ion that is positively (cations) or negatively (anions) charged. A variety of different types of sources for the ions 2 may be employed. Some examples of suitable ion sources include, without limitation, an electrospray ionization (ESI) source, a desorption electrospray ionization (DESI) source, or a sonic spray ionization (SSI) source, an atmospheric pressure chemical ionization (APCI) source, a matrix-assisted laser desprotion/ionization (MALDI) source, and a chemical ionization (CI) source, among others. In some embodiments, the ions 2 may be mass selected before being injected into the ion reaction cell 1, for example, using a quadrupole mass selection device.

The charged species 3 can be electrons or ions that are either positively or negatively charged. When the charged species are electrons, the electron source can be a filament such as a tungsten or thoriated tungsten filament or other electron source such as a $Y_2O_3$ cathode. The reaction device can be filled with a cooling gas, for example, such as helium (He) or nitrogen (N2). The typical pressure of the cooling gas can be between $10^{-2}$ to $10^{-4}$ Torr.

Inside the ion reaction cell 1, the ions 2 and the charged species 3 interact. Depending on the nature of reactants utilized, the interaction can cause a number of phenomena to occur which result in the formation of product ions (fragment ions) 5. The product ions 5 can then be extracted or ejected from the ion reaction cell 1 together with potentially other unreacted ions 2 and/or possibly charged species 3 as the circumstances dictate. The extracted product ions 5 can be guided to a mass analyzer 6. The mass analyzer 6 can include a variety of elements including a detector for detecting the ions and generating information for obtaining a mass spectrum of the product ions 5. A variety of mass analyzers known in the art can be employed. An example of a suitable mass analyzer is a quadrupole time-of-flight mass spectrometer or tandem configuration thereof.

In accordance with various aspects of the applicants' teachings, the exemplary system discussed above with reference to FIG. 1 can be used to analyze one or more ionized isomeric lipids contained within a sample. In accordance with certain aspects of the present teachings, a lipid molecule (M) contained within a sample can be ionized, for example, by reacting the lipid molecule with a cationization agent ($X^+$) so as to form a cationized lipid molecule ($[M+X]^+$). By way of example, the lipid molecule can be protonated so as to form a protonated lipid molecule ($[M+H]^+$). Cationized lipid molecules can alternatively be formed by associating the lipid molecules with a metal ion such as sodium, potassium, silver, or lithium so as to generate a cationized lipid-metal ion adduct such as $[M+Na]^+$, $[M+K]^+$, $[M+Ag]^+$, and $[M+Li]^+$, respectively, all by way of non-limiting example. In accordance with certain aspects of the present teachings, a lipid molecule (M) contained within a sample can be ionized, for example, by deprotonating techniques so as to form an anionized lipid molecule ($[M+H]^-$). Accordingly, in some embodiments, the ions 2 may include cations. In some embodiments, the ions 2 may include anions. In some embodiments, the ions 2 may include singly-charged ions.

In some embodiments, the ions 2 may include cations and the charged species 3 are electrons. Accordingly, the cations may capture the electrons and undergo electron dissociation in which the interaction between ions 2 and charged species 3 results in the formation of product ions (fragment ions) 5 which are fragments of the original ions 2. In some embodiments, the ions 2 may include anions and the charged species 3 are electrons. The anions may capture the electrons and undergo electron dissociation in which the interaction between ions 2 and charged species 3 results in the formation of product ions (fragment ions) 5 which are fragments of the original ions 2. The stream of species ejected from the ion reaction cell may include one or more or a mixture of the ions 2 or the product ions 5 or in some cases, the charged species 3.

In some embodiments, the ion-electron reaction in the ion reaction cell 1 may include electron capture dissociation (ECD), hot electron capture dissociation (HECD), electron transfer dissociation (ETD), electron ionization dissociation (EID), electron-induced excitation of ions in organics (EIEIO), and electron detachment dissociation (EDD). In some embodiments, EIEIO may be used in which electron impact can induce electrical and vibrational excitation of the internal state of molecules resulting in dissociation. In addition, in EIEIO, electrons are not captured by the precursor ions 2 and, as such, EIEIO may be applied to singly-charged molecules. Conventional dissociation techniques, such as ECD may be applied only to multiply charged precursor ions. However, in accordance with applicants' teachings, EID and EIEIO may be applied to the singly-charged precursor ions generated from the samples.

In some embodiments, the ion reaction cell 1 may be configured as a Fourier transform ion cyclotron resonance cell, a digital Paul trap, a linear ion trap, a Chimera trap, or any other type of device or trap configured to facilitate ion-charged species interactions.

In some embodiments, the charged species 3 are electrons. In various aspects, the electrons may have a kinetic energy of about 3 eV, 4 eV, about 5 eV, about 6 eV, about 7 eV, about 8 eV, about 9 eV, about 10 eV, about 11 eV, about 12, eV, about 13 eV, about 14 eV, about 15 eV, about 16 eV, about 17 eV, about 18 eV, about 19 eV, about 20 eV, and any value or range between any two of these values (including endpoints). In various aspects, the electrons may have a kinetic energy of about 4 eV to about 12 eV. In some aspects, the electrons may have a kinetic energy of about 5 eV to about 8 eV.

According to various aspects of applicants' teachings, the kinetic energy of the electrons used to dissociate the precursor ions into fragments was about 4 eV to about 12 eV. Preferably, the kinetic energy of the electrons used to dissociate the precursor ions into fragments was about 5 eV to about 8 eV. For certain types of lipid molecules, EID or EIEIO using electrons having a kinetic energy of about 4 eV to about 12 eV generated fragments conducive to determining structural details thereof, including double-bond locations. If the kinetic energy of the electrons was less than about 3 eV, insufficient dissociation was observed. If the kinetic energy of the electrons was greater than about 12 eV, the increase in dissociation and the resulting fragments lead to spectra that were difficult to analyze and did not produce results of sufficient confidence.

Surprisingly, and as described in more detail below, the use of electron dissociation using electrons with a kinetic energy of about 4 eV to about 12 eV, and particularly about 5 eV to about 8 eV, may fragment lipid molecules to allow for the determination of isomeric species and/or double bond locations within the molecules in accordance with the teachings herein.

Figure 2:
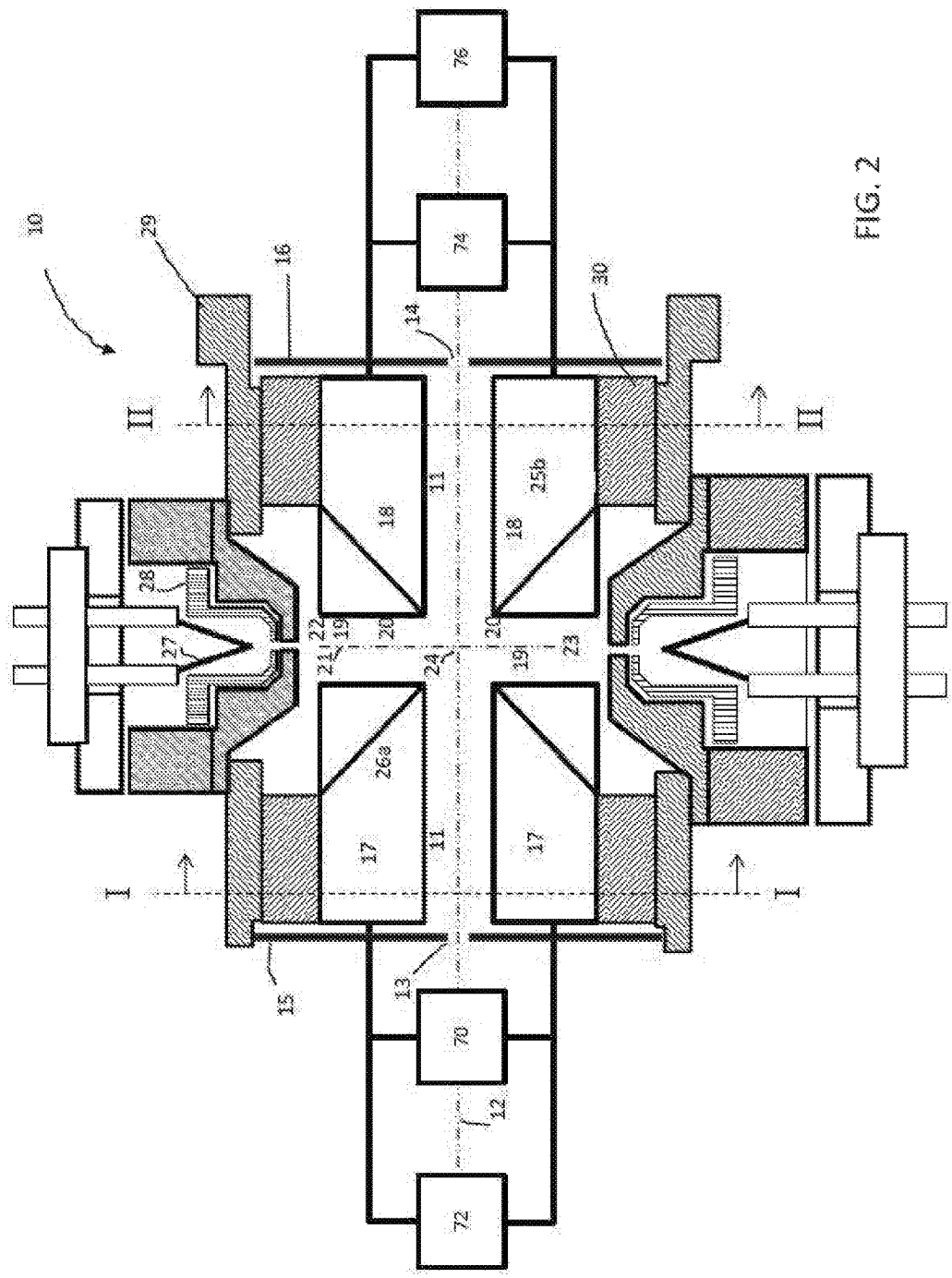
FIG. 2. depicts a cross sectional view in accordance with an embodiment of the invention.

Now referring to FIG. 2, there is depicted a side view of an ion reaction apparatus 10 (a "Chimera" trap) configured to dissociate ions 2 in accordance with an aspect of an embodiment of the invention. The ion reaction apparatus 10 is provided for non-restrictive and illustrative purposes only as any ion reaction apparatus and/or ion reaction cell capable of dissociating ions according to the present teachings.

In FIG. 2, the ion reaction apparatus 10, which is shown as a cut out cross section, includes an outer cylindrical housing 29 and an inner cylindrical housing 30 surround a first pathway 11 having a first central axis 12 and a first axial end 13 and a second axial end 14. This pathway provides a path for ions 2 to enter into the ion reaction apparatus 10. At each end of the first pathway 11 is situated a gate electrode 15, 16. Gate electrode 15 allows ions 2 to enter into the apparatus 10 and gate electrode 16 controls the ejection of unreacted ions 2 or product ions (fragment ions) 5 from the apparatus 10. The gate electrodes need not be situated directly at the axial end, and can be situated just outside and proximate to the axial end. As would be appreciated, due to the symmetrical nature of the device, the direction of the ions can be reversed with ions 2 entering through gate electrode 16 and exiting through gate electrode 15 if surrounding ion transport devices are configured appropriately. The apparatus 10 may include a first set of quadrupole electrodes 17 mounted to the inner cylindrical housing 30, the electrodes 17 being arranged around the first central axis 12 in a quadrupole type arrangement. While quadrupoles are specifically embodied here, any arrangements of multipoles could also be utilized, including hexapoles, octapoles, etc. In the figure, only two of the four quadrupole electrodes are depicted as the other two electrodes are located directly behind the depicted electrodes. Of the two electrodes depicted in the quadrupole electrodes 17, the electrodes have opposite polarity. These first set of quadrupole electrodes 17 are connected to a radio frequency (RF) voltage source 70 and controller 72 which serve to control the voltage source to provide RF voltages to the electrodes to generate an RF field which can guide the ions 2 towards the first central axis 12, the midpoint of the quadrupoles. The controller can include appropriate hardware and software and otherwise be configured as known in the art to apply appropriate signals to the voltage source for applying desired voltages to the electrodes.

A second set of quadrupole electrodes 18 (only two being depicted, as the other two being are located directly behind quadrupole electrodes 18) also being mounted to the inner cylindrical housing 30 is situated at a slight distance away from the first set of quadrupole electrodes 17, the distance forming a mostly cylindrical shaped gap 19 between the first set 17 and second set 18 of electrodes. The first 17 and second 18 quadrupoles share the same central axis 12 and the rods of the first set of quadrupoles 17 are in line with the second set of quadrupoles 18. A quadrupole field may be generated in the gap 19 between the first 17 and second 18 quadrupoles. This second set of quadrupole electrodes 18 is also attached to an RF voltage source 74 and controller 76 which serve to control the voltage source to provide RF voltages to the electrodes to generate an RF field which can serve to guide ions 2 and/or product ions 5 towards the central axis 12, the midpoint of the second set 18 of quadrupole electrodes. The inner and outer cylindrical housing have a cut-out for insertion of a second pathway 20, having a second central axis 21 which has a first axial end 22 and second axial end 23. This second pathway 20 provides a path for the transport of a charged species 3 into the apparatus 10. The first and second pathway are substantially orthogonal to one another and meet at an intersection point 24, this intersection point being along the first 12 and second 21 central axis.

Figure 3B:
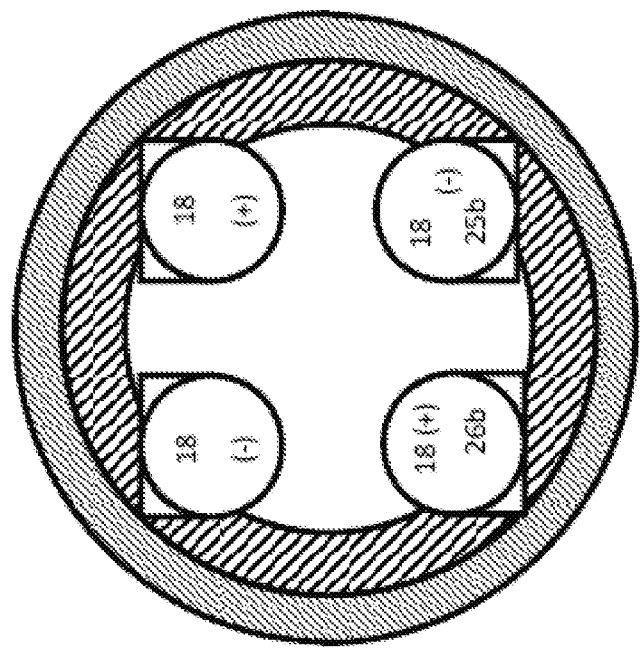
FIG. 3B depicts a cross sectional view of FIG. 2 along the lines II-II
Figure 3A:
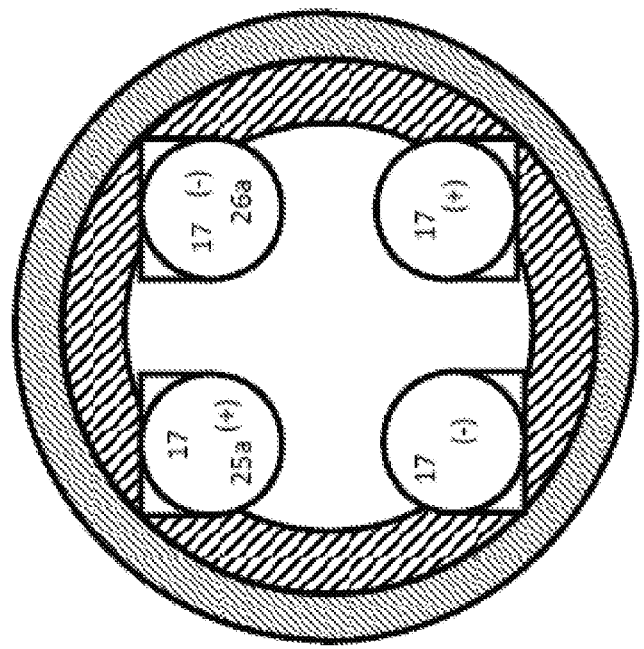
FIG. 3A depicts a cross sectional view of FIG. 2 along the lines I-I

More readily depicted in FIGS. 3A and 3B, which are cross sectional views taken along lines I-I and II-II of FIG. 2 respectively, each of the four electrodes in the first set of quadrupole electrodes 17 can be paired with one of the four electrodes in the second set of electrodes 18, such as for example wherein each electrode 25a, 25b in each electrode pair has the opposite polarity and is directly opposite across the intersection point of the other electrode 25b, 25a in the electrode pair, respectively. A similar relationship exists for the electrode pair with electrodes 26a, 26b. The same relationship applies to the two remaining electrodes in the first set of electrodes 17 pairing with the two remaining electrodes in the second set of electrodes 18. This orientation of the electrodes causes the RF fields that are generated between the intersection point 24 and the first axial end 22 of the second pathway 20 to be in reverse phase to the RF field generated between intersection point 24 and second axial end 23 of second pathway 20. Because of this configuration of the electrodes, no RF field is present on the center axis 21. The first axial end 22 of the second pathway 20 contains or has proximate to it, an electron filament 27 to be used to generate electrons for transmission into the second pathway 20 towards the intersection point 24. The first axial end 22 can also contain or have proximate to it, a suitable electrode gate 28 to control the entrance of electrons into the apparatus 10. A magnetic field source (not shown), such as a permanent magnet may be configured to implement a magnetic field that is parallel to the second pathway 20. This magnetic field is useful when ECD, hot ECD, EID, EDD, EIEIO and negative ECD are being implemented where the charged species are electrons. The RF frequencies applied to the quadrupoles may be in the range of about 400 kHz to 1.2 MHz, preferably the RF frequency is around 800 kHz.

In accordance with certain aspects of the present teachings, the ion reaction apparatus 10 ("Chimera" trap) may be in fluid communication with and/or located within a gas container connected to a gas source (not shown). Non-limiting examples of gas include oxygen, nitrogen, and hydrogen. Although oxygen gas may be used as an example herein, embodiments are not so limited as the gas may be any type of gas capable of operating according to some embodiments. In various aspects, the oxygen gas may be introduced to react with radical fragments of the product ions generated within the ion reaction apparatus 10. For example, a radical fragment [fragment.]$^+$ may react with the oxygen gas to generate an oxygenated fragment [fragment.+ $O_2$]$^+$. In some embodiments, the flow of oxygen gas may be controlled by a pulse valve as known to those having ordinary skill in the art. In some embodiments, the oxygen gas may be pulsed for about 1 millisecond to about 100 milliseconds. In an alternative embodiment, the oxygen gas may be introduced downstream of the ion reaction apparatus 10, such as in an ion trap of the mass spectrometer. The oxygen-radical fragment reaction may be controlled through the pulse valve and/or through a certain voltage within the ion reaction apparatus 10 and/or downstream device to control travel time of the fragments through the oxygen gas. For example, traveling time through an ion trap may be controlled using a linear acceleration (LINAC) voltage. In an example where no oxygen-radical fragment reaction is required, a fast extraction or travel time may be implemented by applying a high LINAC voltage. In an alternative example in which promotion of the oxygen-radical fragment reaction is required, a slower extraction or travel time may be implemented by applying a low (or no) LINAC voltage.

Figure 4:
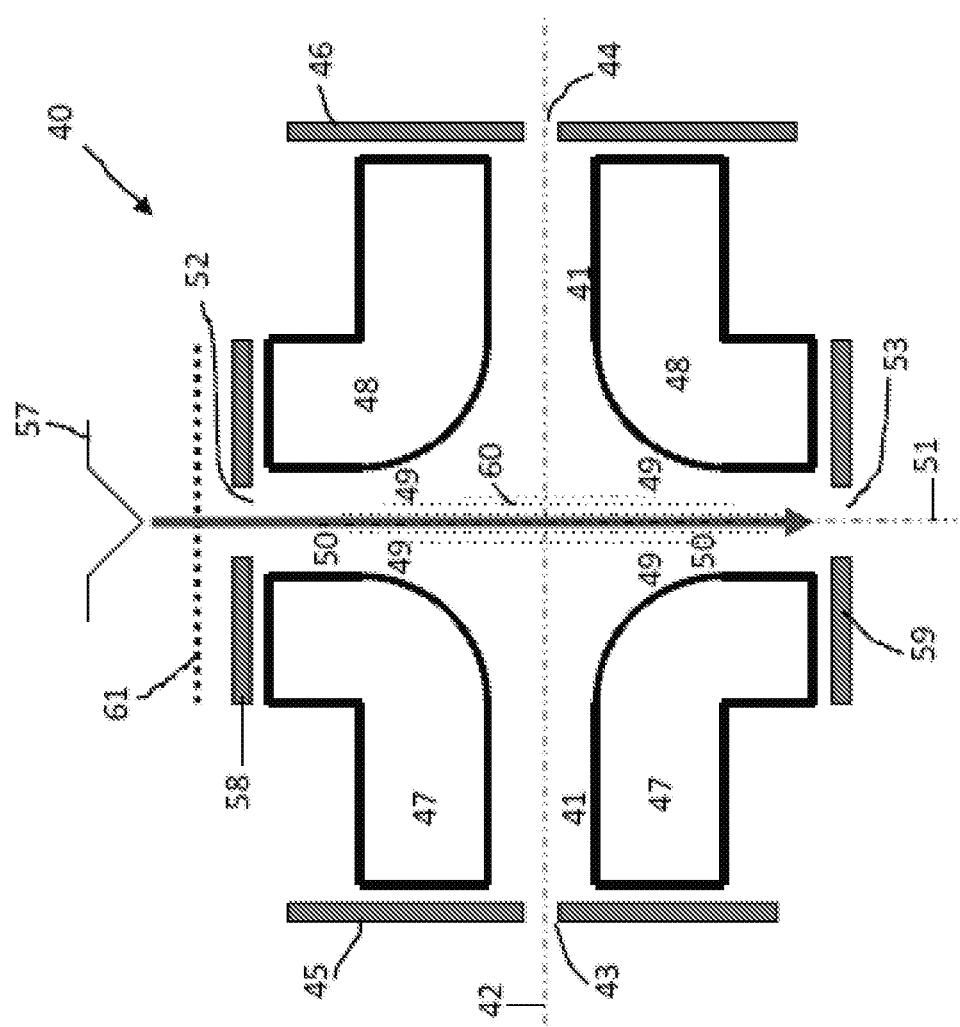
FIG. 4 depicts a simplified side view of an example of electron injection in accordance with an embodiment of the invention

Now referring to FIG. 4, a depiction of another embodiment in side view of the ion reaction device 40 is shown in which only a charged species 3, specifically electrons, are injected. The ion reaction device 40 contains a first pathway 41 having a first central axis 42, the pathway 41 has a first axial end 43 and a second axial end 44. At each end of the first pathway 41 is situated an electrode gate 45, 46 which allows for the control of the entrance and ejection of ions from the ion reaction device 40. The apparatus 40 may include a first set of quadrupole electrodes 47, generally L-shaped, arranged around the first central axis 42. In FIG. 4, only two of the four quadrupole electrodes are depicted, the other two electrodes are directly behind the depicted electrodes. Of the two electrodes depicted in the quadrupole electrodes 47, the electrodes have opposite polarity. A second set of quadrupole electrodes 48 (only two being depicted, the other two being directly behind), also generally L-shaped is situated at a slight distance away from the first set of quadrupole electrodes 47, the distance forming a solid mostly cylindrical shaped gap 49 between the first set 47 and second set 48 of electrodes. Of the two electrodes depicted in the quadrupole electrodes 48, the electrodes have opposite polarity. The top depicted electrode in each of the first set 47 and second set 48 of quadrupole electrodes are opposite in polarity to one another. As would be understood by the skilled person, the two electrodes not shown of each set of quadrupole electrodes would have polarities consistent with quadrupole electrode polarities, such as for example the configuration shown in FIGS. 3A and 3B.

A second pathway 50 has a second central axis 51 which has a first axial end 52 and second axial end 53. This second pathway provides a path for the transport of a charged species into the apparatus 40. This orientation of the electrodes results in the RF fields that are generated between the intersection point (of the first pathway 41 and second pathway 50) and the first axial end 52 of the second pathway 50 to be in reverse phase to the RF field generated between the intersection point (of the first pathway 41 and second pathway 50) and said second axial end 53 of said second pathway 50. The first axial end 52 of the second pathway 50 contains or has situated proximate to it, an electron filament 57 to be used to generate electrons 60 for transmission into the second pathway 50. The first axial end 52 can also contain or have situated near and proximate to it, a suitable electrode gate 58 to control the entrance of electrons 60 into the apparatus 40. Another gate electrode 59 is present or situated proximate to the second axial end 53 of the second pathway 50.

A magnetic field generator (not shown) is positioned and oriented in such a way so as to create a magnetic field parallel to the second pathway. The direction of the magnetic field can be either from the first axial end 52 to the second axial end 53 or vice versa. This magnetic field is useful when ECD, hot ECD, EID, EDD, EIEIO and negative ECD are being implemented where the charged species are electrons. In some embodiments in which the charged species are reagent anions and include, for example the scenario where the reaction taking place is an ETD reaction, the magnetic field source and magnetic field are not needed. A grid 61 can be positioned to act as a gate to control the flow of the electrons 60 near or proximate to the electron filament 57. The RF fields causes the electrons 60 that are focused as they enter the apparatus 40 to become defocused as they approach the intersection point of the first pathway 41 and second pathway 50. As the electrons 60 pass the intersection point, the reversal in polarity of the RF fields causes the electron 60 to become focused again. This creates a more uniform distribution of electrons normal to the first pathway and increases the chances of ion-electron interactions in the apparatus 40 which can also result in better sensitivity. The electron beam creates a localized attractive potential.

In accordance with the present teachings, a reaction apparatus configured according to some embodiments may operate in various modes of operation. In a continuous mode of operation, a stream of ions is introduced continuously into the reaction apparatus at one end and electrons are introduced into the reaction apparatus in a stream that is orthogonal to the stream of ions. Gates situated at the entrance and exit of both the ion pathway and the electron pathway are continuously open. Upon interaction of the ions with the electrons, some of the ions undergo EID or EIEIO and fragment. The product ions which include the fragmented portions, as well as unfragmented precursor ions are then continuously extracted from the reaction apparatus to be subsequently processed and analyzed using an ion detector.

In a semi-continuous mode, the apparatus is configured such that the entrance gate of the ion pathway is continuously open, whereas the exit gate of the ion pathway switches between an open and closed position. The entrance gate for the electron pathway can be opened continuously. When the exit gate of the ion pathway is in a closed position, ions are unable to exit the apparatus through the exit gate and an accumulation of ions takes place within the apparatus. Electrons which are continuously entering the apparatus orthogonally to the incoming ion stream interact with the ions as they accumulate, some of the ions undergoing EID or EIEIO to fragment. Once a sufficient amount of time has passed, the exit gate of the ion pathway is then opened to allow a removal of the product ions and unreacted ions that have accumulated. These exiting ions can then be further processed and/or manipulated in subsequent stages and/or analyzed using an ion detector.

In trapping (or "batch") mode the apparatus is utilized in a manner in which the entrance and exit gates are operated in a fashion to allow ions into the apparatus in a non-continuous mode. Entrance gate of the ion pathway is open and exit gate of the ion pathway is closed and ions are transmitted through the entrance gate into the apparatus. During this time period, entrance gate of the electron pathway is closed. Once sufficient ions are accumulated within the apparatus, the entrance gate of the ion pathway is closed and entrance gate to the electron pathway is opened allowing electrons to enter into the apparatus where they can interact with the accumulated ions and cause a dissocation reaction (e.g, ECD, EID, EIEIO, etc.) to fragment the ions. Once a sufficient period of time has passed for the reaction, the electron entrance gate can be closed or the electron beam can be turned off and the exit gate of the ion pathway is opened to allow extraction of the fragmented product ions or unreacted precursor ions which can then be further processed and/or manipulated and/or analyzed using an ion detector. The duration of time in which the ion exit gate is closed and in which the ions interact with the electrons can be predetermined as a function of the charge state of the original precursor ions, or can set manually based on experience.

The apparatus may be integrated into a mass spectrometer or tandem mass spectrometer as known to those having ordinary skill in the art. A non-limiting example of a mass spectrometer in which the present teachings can be incorporated is a quadrupole time-of-flight mass spectrometer. The apparatus may be used to analyze various types of samples dissociated using techniques described herein, including samples containing or suspected of containing lipid molecules.

EXAMPLES

The applicants' teachings can be even more fully understood with reference to the following examples and data presented in FIGS. 5-8, which demonstrate the analysis of isomeric lipids present in a sample and/or the location of double bonds in analyzed molecules by analyzing dissociated fragments (i.e., fragment ions) dissociated in accordance with various aspects of the teachings herein. Other embodiments of the applicants' teachings will be apparent to those skilled in the art from consideration of the present specification and practice of the present teachings disclosed herein. It is intended that these examples be considered as exemplary only.

Samples containing or suspected of containing lipids ("samples") were ionized to generate singly-charged precursor ions. The precursor ions were mass selected and dissociated into fragments (fragment ions) as discussed in more detail below.

Example 1: Determining Double Bond Location

Figure 5:
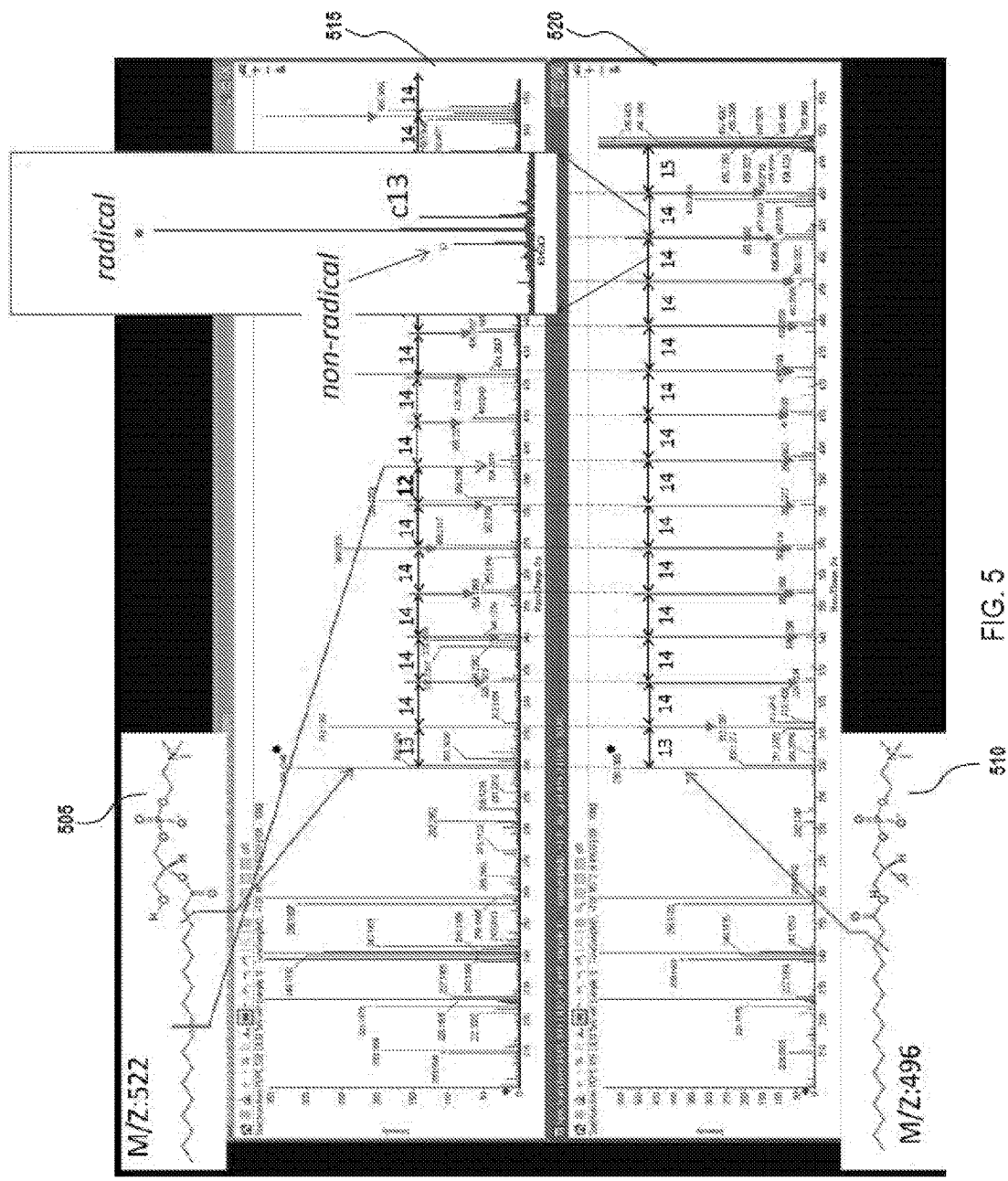
FIG. 5 depicts data for lipid species dissociated and subsequently detected in accordance with aspects of various embodiments of the applicants' teachings.

With reference to FIG. 5, a sample included precursor ions for a first species 505 having a m/z of about 522 amu and a second species 510 having an m/z of about 496 amu. The first species 505 and the second species 510 may be found as contaminations of a POPC sample. The precursor ions were subjected to EIEIO, which led to the formation of fragments or fragment ions. The alkyl chains for each of the first species 505 and the second species 510 was reconstructed using each species' respective spectra 515,520 starting at the peak corresponding with an m/z of 299 amu. The arrows in the spectra 515, 520 represent non-radical species and the neighbor peaks at the arrows +H (or +1) indicate radical species. The radical species were produced by EIEIO and the non-radical species were formed by H. loss reaction. Each peak is made of three individual peaks: a non-radical peak, a radical peak, and a (carbon) C13 peak.

As shown in spectra 520, 14 amu spacing was observed for the second species 510 indicating that the alkyl chain did not have any double bonds, which is comparable to the known structure of the second species 510. As shown in spectra 515, one 12 amu spacing was observed indicating the location of a double bond. This position of the double-bond corresponds with the known structure of the first species 505.

Example 2: Determining Double Bond Location in a Double-Alkyl Chain Molecule (POPC)

Figure 6:
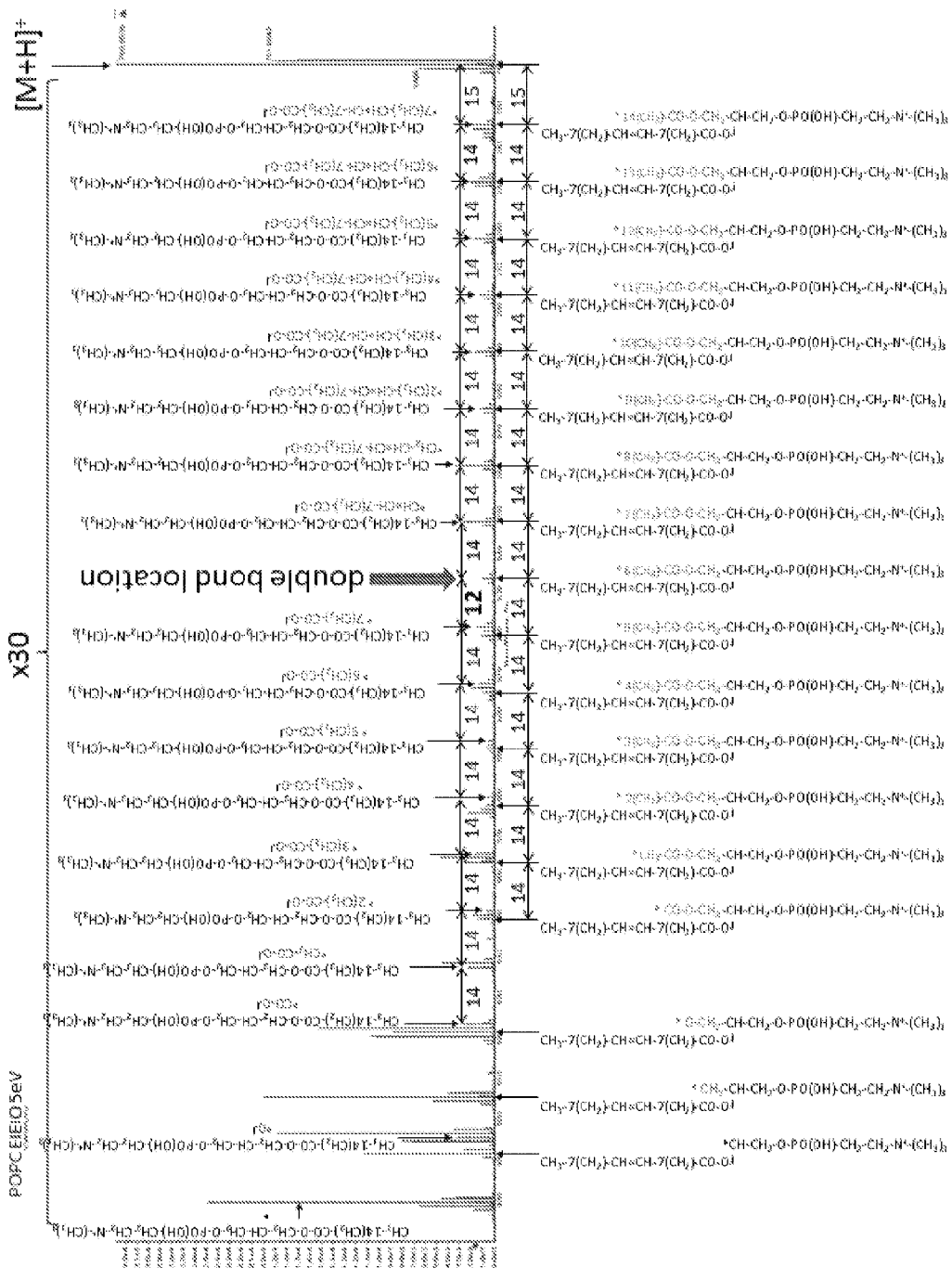
FIG. 6 depicts data for alkyl chain fragments (fragment ions) that were dissociated from a POPC molecule and subsequently detected in accordance with aspects of various embodiments of the applicants' teachings.

FIG. 6 depicts a spectra of a sample containing POPC dissociated using EIEIO. POPC contains two alkyl chains, one of which has a double bond. An electron may dissociate one of the alkyl chains. The resulting EIEIO spectrum depicted in FIG. 6 indicate the presence of two series of fragments. If there is no double bond in the alkyl chains, the spectrum profile will include 14 amu spacing for both radical fragments and non-radical fragments. A local spectrum profile will include twin peaks for the radical fragments and non-radical fragments. If there is a double bond in the alkyl chain, the spacing at this location will be 12 amu for both radical fragments and non-radical fragments. As depicted in FIG. 6, 12 amu spacing was observed at the double bond location.

Example 3: Reaction of Oxygen Gas with Radical Fragments

Figure 7:
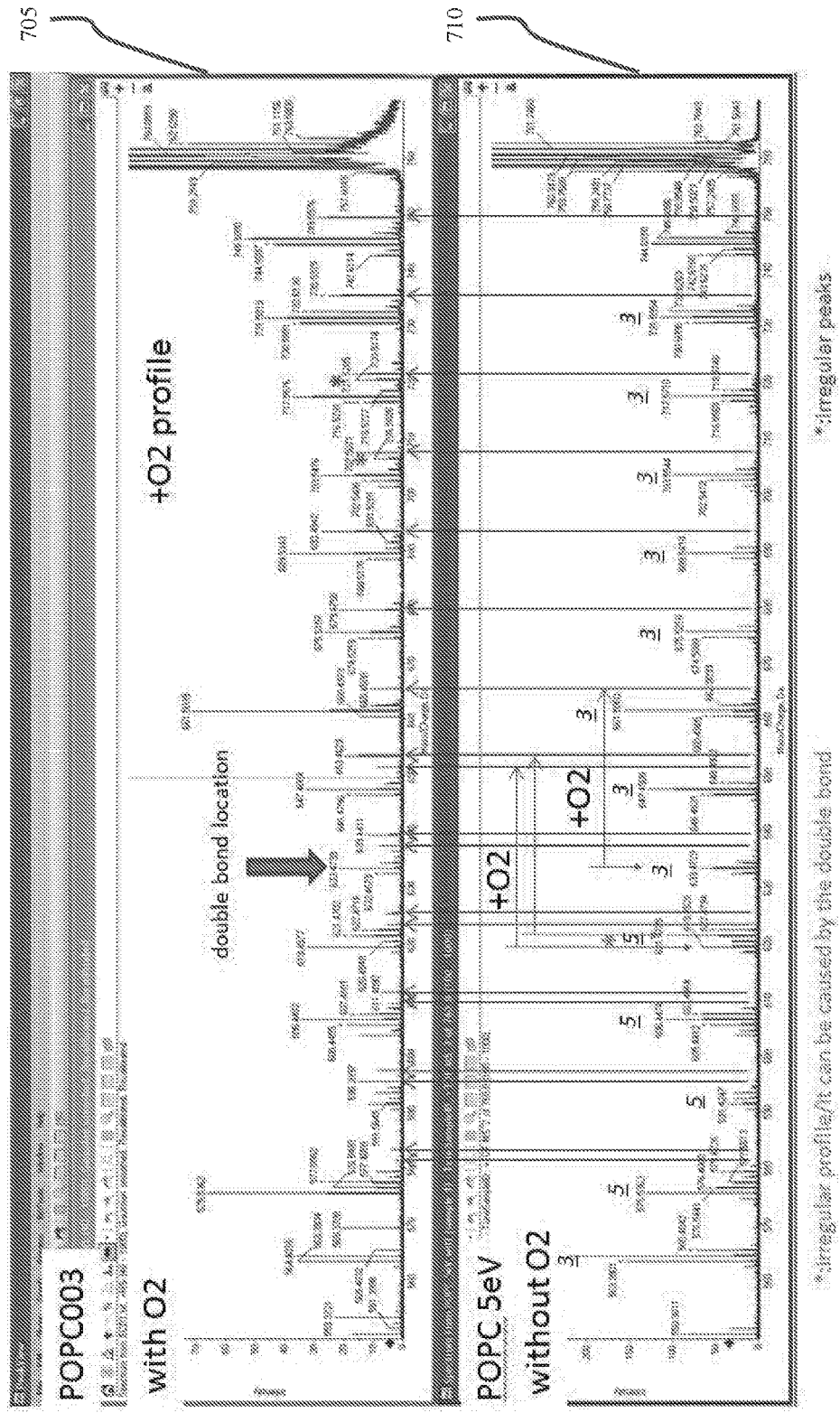
FIG. 7 depicts data for a POPC sample dissociated and subsequently detected in accordance with aspects of various embodiments of the applicants' teachings with and without radical fragment reaction with oxygen gas before detection.

Referring now to FIG. 7, therein is depicted spectra of a sample containing POPC dissociated using EIEIO to generate radical fragments. In a first spectra 705, the radical fragments were not reacted with oxygen and in a second spectra 710 the radical fragments were reacted with oxygen gas to generate oxygen-radical fragments. The oxygen may react with radical fragments of POPC alkyl chains dissociated using techniques described herein, including EIEIO. The spectra 705, 710 include local peak profiles having a radical peak and a non-radical peak (as in Examples 1 and 2, above). As shown in spectra 705, the oxygen-radical fragments generated additional peaks, indicating that the fragment is a radical. The oxygen-radical fragment appears as a +32 amu adduct relative to the radical fragment peak that has not reacted with oxygen. For the POPC sample in spectra 710, the oxygen-radical fragments from the single bond chain showed a 14 amu spacing, while the double bond location of the double bond from the double bond chain showed 12 amu spacing at the double bond location. As a result, the oxygen-radical fragment profile showed a peak split at the double bond location.

Example 4: POPC and OPPC Identification

Figure 8:
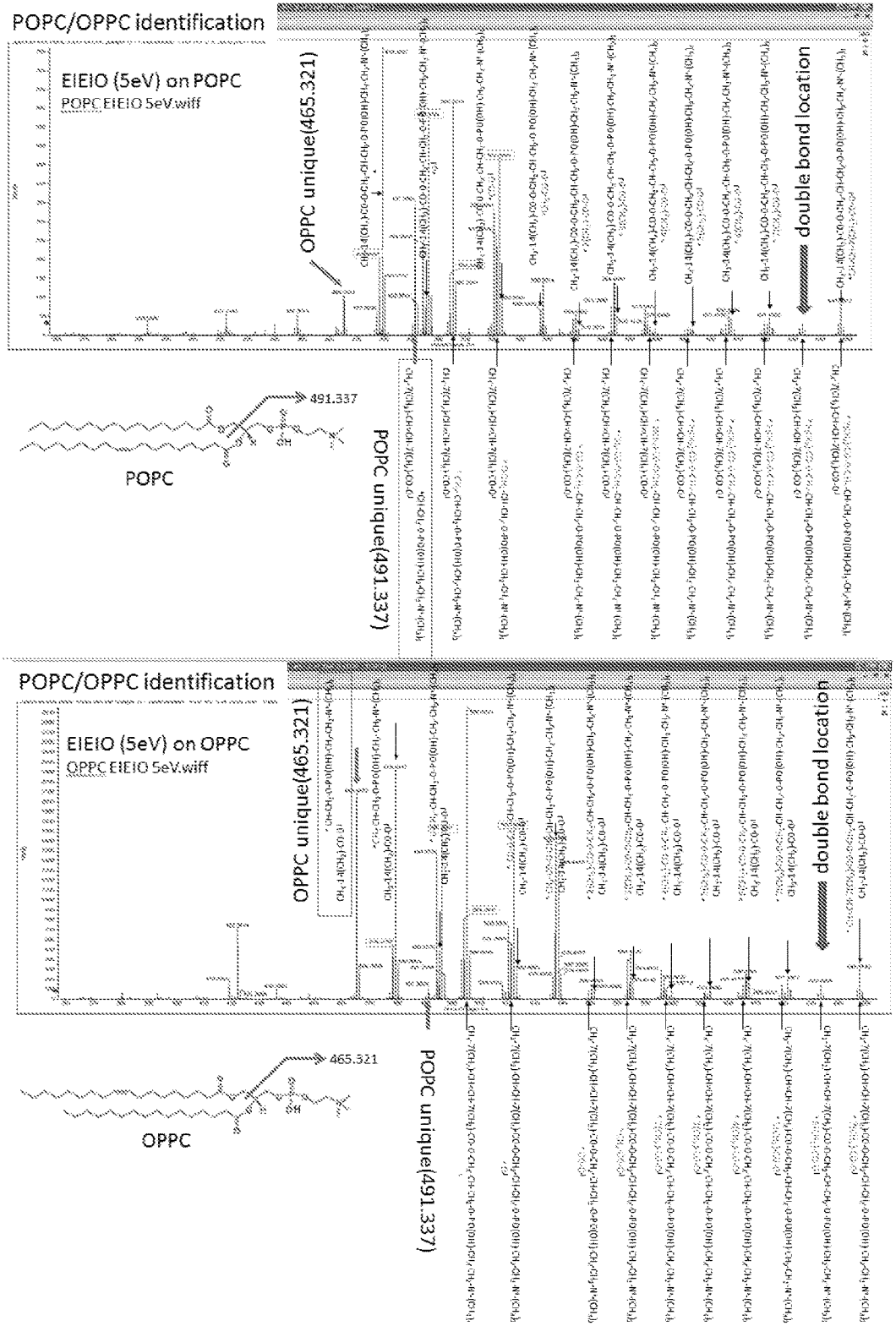
FIG. 8 depicts data for a POPC and OPPC mixture dissociated and subsequently detected in accordance with aspects of various embodiments of the applicants' teachings.

A sample containing a mixture of POPC and OPPC was prepared and analyzed according to some embodiments. The sample was ionized to produce POPC and OPPC precursor ions that were dissociated using EIEIO. As shown in FIG. 8, EIEIO cleaved most of the carbon-carbon bonds along the alkyl chains, including the POPC unique fragment (m/z: 491.337) and the OPPC unique fragment (m/z: 465.321). The relative intensity ratio of these unique peaks indicates the relative abundance of POPC and OPPC. For example, for an OPPC sample, the OPPC unique fragment was observed predominately compared with the POPC unique fragment. In another example, for a POPC sample, the POPC unique fragment was observed predominately compared with the OPPC unique fragment. In comparison with conventional dissociation techniques, such as CID, only four fragments would have been observed over the same range as the spectra depicted in FIG. 8.

Surprisingly, these data demonstrate that the use of electron dissociation using electrons with a kinetic energy of about 4 eV to about 12 eV may fragment lipid molecules to allow for the determination of isomeric species and/or double bond locations within the molecules in accordance with the teachings herein.

Example 5: Phospholipid Identification

Figure 9:
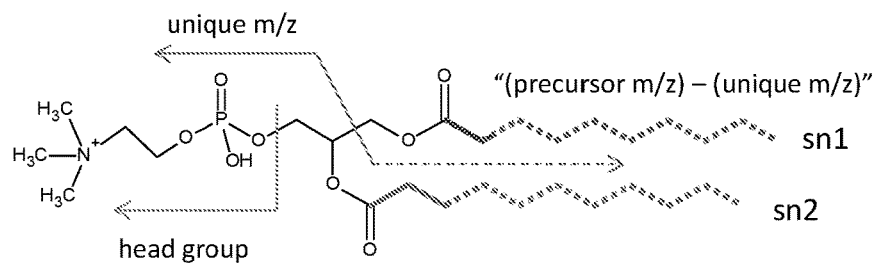
FIG. 9 depicts a manner in which phospholipid identification can be performed in accordance with various embodiments of the applicants' teachings.

More universally, generalized phospholipids can also be identified using the teachings described in the present application, specifically utilizing the EIEIO approach. The table provided in FIG. 9 shows the m/z value of the diagnostic peak for many types of phospholipids including OPPC and POPC. The head group of phospholipids can be identified by peaks with lower m/z values, which often appears as an intense peak. For example, existence of a peak with an m/z value of 184.073 indicates that the phospholipid is a Phosphatidylcholine (PC). In another example, the existence of a peak with an m/z value of 142.026 indicates that the phospholipid is a Phosphatidylethanolamine (PE). Existence of a peak with an m/z value of 207.998 indicates that the phospholipid is a Phosphatidylserine (PS) and this species is charged by a sodium ion. Existence of a peak with an m/z value of 238.019 indicates that the phospholipid is a Phosphatidylinositol (PI) and this species is charged by a sodium ion. These m/z values are theoretically given by dissociation between oxygen and carbon at the sn3 location, (indicated by the noted "headgroup" loss shown in the molecule depicted in FIG. 9). Using this rule, diagnostic m/z for other phospholipids and charging species (i.e., proton, sodium, potassium, and other metallic ions) are calculated. Once the phospholipid head group is identified, one of the sn2 diagnostic mass with the identified head group will be found in the spectrum. In case that m/z 491.337 is found with the head group of PC, acyl chain at sn-2 position is identified as 18:1, i.e., the acyl chain has 18 carbons as the chain and it contains one double bond. To identify acyl chain at the sn-1 position, "(precursor m./z)−(sn-2 diagnostic m/z)" is calculated and this value will be found in the table 1. The found value indicate the acyl chain at the sn-1 position.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

What is claimed is:

1. A method for analyzing a sample containing or suspected of containing at least one lipid using a mass spectrometer, the method comprising:
   ionizing the sample to form a plurality of parent ions;
   performing an electron dissociation reaction to fragment at least a portion of the plurality of parent ions into a plurality of daughter ions, the electron dissociation reaction comprising irradiating the plurality of parent ions with electrons; wherein the electrons have a kinetic energy of 8 electron Volts to 12 electron Volts; and
   detecting at least a portion of the plurality of daughter ions at a detector of the mass spectrometer to form at least one spectrum for mass analysis of the sample.

2. A method for analyzing a sample containing or suspected of containing at least one lipid using a mass spectrometer, the method comprising:
   ionizing the sample to form a plurality of singly-charged precursor ion species;
   performing an ion-electron reaction to fragment at least a portion of the plurality of precursor ion species into a plurality of product ion species, the ion-electron reaction comprising irradiating the plurality of precursor ions with electrons having a kinetic energy of 4 electron Volts to 12 electron Volts; and
   detecting at least a portion of the plurality of product ion species at a detector of the mass spectrometer to form at least one spectrum for mass analysis of the sample.

3. The method of claim 2, wherein the ion-electron reaction comprises at least one of electron capture dissociation, hot electron capture dissociation, electron transfer dissociation, electron ionization dissociation, electron-induced excitation in organics, and electron detachment dissociation.

4. The method of claim 2, wherein the ion-electron reaction comprises electron ionization dissociation.

5. The method of claim 2, wherein the ion-electron reaction comprises electron-induced excitation in organics.

6. The method of claim 2, wherein the ion-electron reaction occurs in at least one of a Fourier transform ion cyclotron resonance cell, a digital Paul trap, a linear ion trap, and a Chimera trap.

7. The method of claim 2, wherein the at least one lipid comprises at least two isomeric species.

8. The method of claim 1, wherein the at least two isomeric species comprise OPPC and POPC.

9. The method of claim 8, wherein the plurality of fragment ions includes at least one alkyl chain fragment.

10. The method of claim 2, wherein peaks in the at least one spectra associated with the plurality of daughter ions and exhibiting a regular spacing indicate that said at least one lipid includes double bonds.

11. The method of claim 10, wherein a 14 atomic mass unit spacing indicates a single bond of the at least one lipid and a 12 atomic mass unit spacing indicates a double bond of the at least one lipid.

12. The method of claim 2, wherein the plurality of fragment ions comprise radical fragments and non-radical fragments.

13. The method of claim 2, further comp ng introducing gas to react with radical fragments of the plurality of fragment ions.

14. The method of claim 2, wherein the gas includes at least one of oxygen gas, nitrogen gas, and helium gas.

15. The method of claim 14, wherein the gas is introduced within an ion-electron reaction device.

16. The method of claim 14, wherein the gas is introduced downstream of an ion-electron reaction device.

17. The method of claim 14, wherein the gas is introduced for 1 millisecond to 100 milliseconds.

18. A reaction apparatus for ions comprising:
   a first pathway comprising a first axial end and a second axial end disposed at a distance from the first pathway axial end along a first central axis;
   a second pathway comprising a first axial end and a second axial end disposed at a distance from the first axial end of the second pathway along a second central axis;
      said first and second central axis being substantially orthogonal to one another and having an intersection point;
   a first set of quadrupole electrodes arranged in a quadrupole orientation around said first central axis and disposed between said first axial end of said first pathway and said intersection point, said first set of electrodes for guiding ions along a first portion of said first central axis;
   a second set of quadrupole electrodes arranged in a quadrupole orientation around said first central axis and disposed between said second axial end of said first pathway and said intersection point, said second set of electrodes being configured for guiding ions along a second portion of said first central axis;
      the first set of electrodes being separated from the second set of electrodes so as to form a gap transverse to said first central axis;
   a voltage source for providing an RF voltage to said first and second sets of electrodes to generate an RF field;
   a controller for controlling said RF voltages;
   a lipid ion source disposed at or proximate either the first or second axial end of said first pathway for introducing lipid ions along said first central axis towards the other of said first or second axial end of the first pathway; and
   a charged species source disposed at or proximate either the first or second axial end of the second pathway for introducing electrons having a kinetic energy of 4 electron Volts to 12 electron Volts along the second central axis, said charged species travelling through said gap towards said intersection point.

19. The apparatus of claim 18, wherein the at least one lipid comprises at least two lipid isomers and optionally wherein the at least two lipid isomers comprise OPPC and POPC.

20. The method of claim 2, wherein the electrons have a kinetic energy of 8 electron Volts to 12 electron Volts.

21. The method of claim 7, wherein the at least two isomeric species comprise OPPC and POPC.

* * * * *